United States Patent
Hayes et al.

(10) Patent No.: US 9,922,533 B2
(45) Date of Patent: Mar. 20, 2018

(54) SYSTEM AND METHOD OF MANAGING THE CLEANING OF A MEDICAL APPARATUS

(71) Applicant: Stryker Corporation, Kalmazoo, FL (US)

(72) Inventors: Michael Joseph Hayes, Kalamazoo, MI (US); Anuj K. Sidhu, Kalamazoo, MI (US)

(73) Assignee: Stryker Corporation, Kalamazoo, MI (US)

(*) Notice: Subject to any disclaimer, the term of this patent is extended or adjusted under 35 U.S.C. 154(b) by 0 days.

(21) Appl. No.: 14/947,637

(22) Filed: Nov. 20, 2015

(65) Prior Publication Data

US 2016/0148485 A1 May 26, 2016

Related U.S. Application Data

(60) Provisional application No. 62/082,687, filed on Nov. 21, 2014.

(51) Int. Cl.
| | |
|---|---|
| *G08B 21/00* | (2006.01) |
| *G08B 21/24* | (2006.01) |
| *A61L 2/26* | (2006.01) |
| *A61L 2/28* | (2006.01) |

(52) U.S. Cl.
CPC ............ *G08B 21/245* (2013.01); *A61L 2/26* (2013.01); *A61L 2/28* (2013.01); *A61L 2202/14* (2013.01); *A61L 2202/24* (2013.01); *A61L 2202/26* (2013.01)

(58) Field of Classification Search
CPC ............ G07C 9/00309; G07C 9/00896; H04L 63/0421
USPC ............................................. 340/561
See application file for complete search history.

(56) References Cited

U.S. PATENT DOCUMENTS

| | | | |
|---|---|---|---|
| 2008/0172789 A1* | 7/2008 | Elliot ................... | A61G 7/0528 5/616 |
| 2012/0116803 A1* | 5/2012 | Reid ..................... | A61L 2/28 705/2 |
| 2015/0128352 A1* | 5/2015 | Papaioannou ....... | A61G 7/0573 5/699 |
| 2015/0351982 A1* | 12/2015 | Krenik ................. | A47C 23/06 5/616 |

* cited by examiner

*Primary Examiner* — Tanmay Shah
(74) *Attorney, Agent, or Firm* — Warner Norcross & Judd LLP

(57) ABSTRACT

A surface cleaning assistance system includes a surface and a sensor mounted relative to the surface. The sensor is configured to detect pressure applied to the surface and generates sensor signals based on the detected pressure. The system also includes a controller in communication with the sensor and has stored therein a cleaning target value. The controller is configured to receive the sensor signals from the sensor, to compare the sensor signals to the cleaning target value, and to generate an output signal associated with the sensor signals, the output signal indicating whether the sensor signals indicate a pressure below, at, or above the cleaning target value.

18 Claims, 7 Drawing Sheets

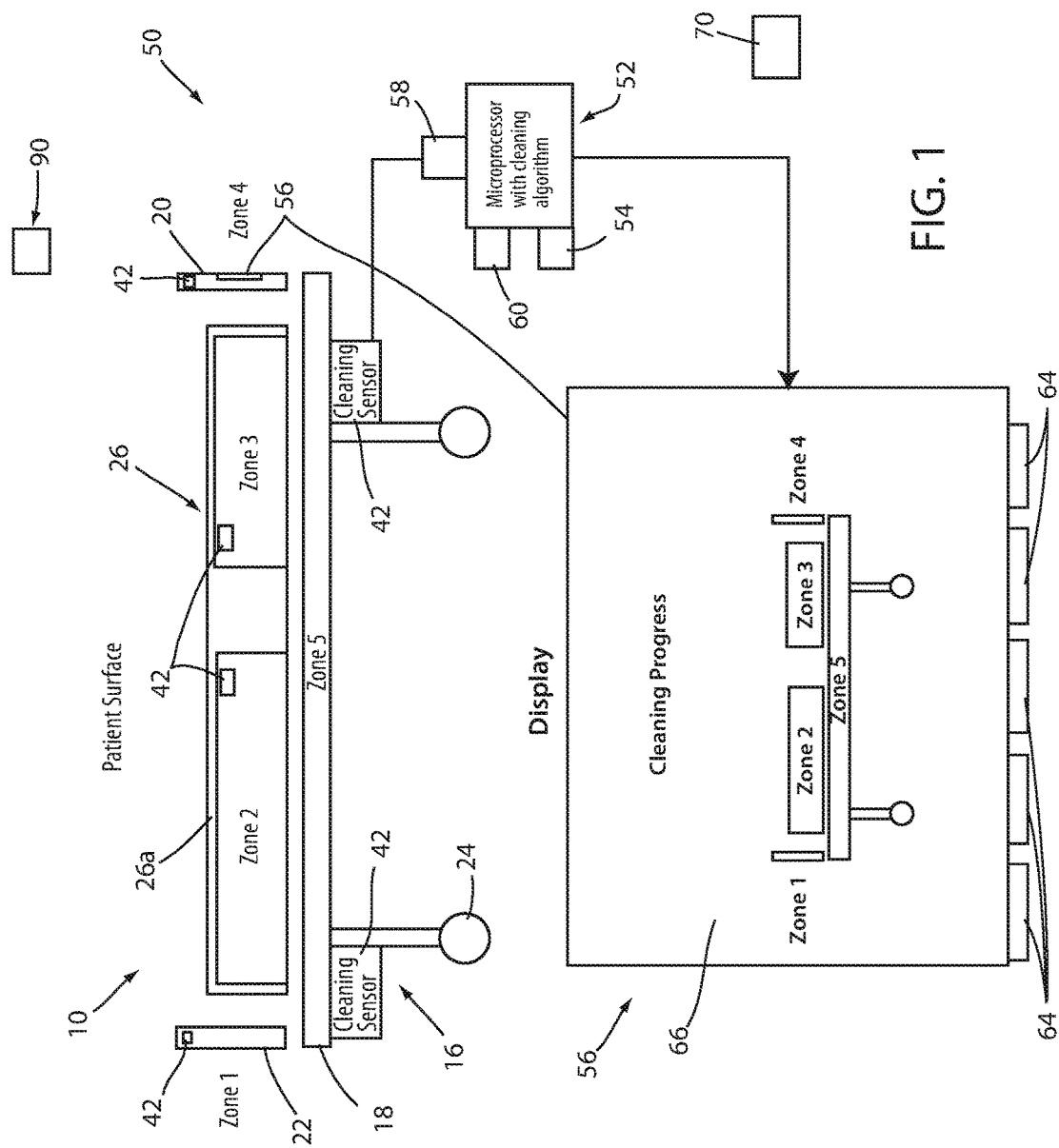

SYSTEM AND METHOD OF MANAGING THE CLEANING OF A MEDICAL APPARATUS

RELATED APPLICATIONS

This application claims the benefit of U.S. Provisional Patent Application Ser. No. 62/082,687, filed Nov. 21, 2014, which is incorporated herein by reference in its entirety.

BACKGROUND

The present invention relates to a system and method of managing the cleaning of a medical apparatus or equipment—such as a bed, a stretcher, a cot, a medical chair, a temperature management device, and other medical equipment and devices—and, more particularly, to a method that monitors, trains, provides feedback, and/or tracks the cleaning of a medical apparatus.

Infection control is a continuing concern for most healthcare facilities. Hospital staff typically wipe down an apparatus surface with cleaning solvents. As they move around the surface, areas can easily be missed. While great strides have been made with equipment and cleaning solutions that, when properly used, can effectively clean a variety of surfaces found in healthcare facilities, quite often the equipment or solutions are not properly used and, further, may lead to cross-contamination.

SUMMARY OF THE INVENTION

The present invention provides systems and methods for managing the cleaning of medical apparatus or equipment by monitoring, providing feedback, training, and/or tracking of the cleaning process.

In one embodiment, a surface cleaning assistance system includes a surface and a sensor mounted relative to the surface. The sensor is configured to detect pressure applied to the surface and generates sensor signals based on the detected pressure. The system also includes a controller in communication with the sensor and has stored therein a cleaning target value. The controller is configured to receive the sensor signals from the sensor, to compare the sensor signals to the cleaning target value, and to generate an output signal associated with the sensor signals, the output signal indicating whether the sensor signals indicate a pressure below, at, or above the cleaning target value.

In one aspect, the surface comprises a surface of an apparatus. For example, the apparatus may comprise a medical apparatus, such as a hospital bed, a stretcher, an OR table, a cot, or a medical recliner.

In one embodiment, the medical apparatus comprises a hospital bed. The surface cleaning assistance system further comprises a display at the hospital bed, with the display in communication with the controller and generating an image, and with the image being responsive to the output signal.

For example, the image may comprise a map of at least a portion of the hospital bed.

In yet another embodiment, the sensor comprises a first sensor, and the system includes a second sensor. The controller is in communication with the sensors and evaluates the sensor signals from each of the sensors.

For example, each of the sensors may be associated with a discrete region or area of the surface.

In one embodiment, the map is segmented into zones. Each zone corresponds to and has an icon representing one region of the surface.

In a further aspect, the controller changes the icon associated with the one region when the controller determines that the sensor signals associated with the one region indicates for the one region changes in pressure from below, at, or above the target value for the one region.

In another embodiment, the system includes a display. The display is in communication with the controller and generates an image, which changes in response to the output signal.

In another embodiment, the system includes a transmitter, which is in communication with the controller for sending the output signal from the controller to a remote device.

In one embodiment, the sensor comprises a load cell.

In another embodiment, the system includes a user interface. The user interface is in communication with the controller and configured to initiate the controller monitoring the sensor signals.

In another embodiment, the system includes a timer. The controller includes or is in communication with the timer. The controller determines the time spent by a user cleaning the surface using the timer.

In yet another embodiment, the system further includes a camera, the camera which monitors the surface. The camera is in communication with the controller.

According to yet another embodiment, a surface cleaning assistance system includes a surface sensor mounted relative to the surface. The sensor is configured to detect movement across the surface and generates sensor signals based on the detected movement across the surface.

The system further includes a controller in communication with the sensor. The controller has stored therein a cleaning target area. The controller is configured to receive the sensor signals from the sensor and to compare the detected movement to the cleaning target area and further generate an output signal associated with the sensor signals. The output signal indicates whether the sensor signals indicate the movement covers or does not cover the cleaning target area.

In one embodiment, the surface comprises a surface of an apparatus, such as a medical apparatus, including a hospital bed, a stretcher, an OR table, a medical recliner, or a cot.

In another embodiment, the system includes a display in communication with the controller. The display displays an image based on the output signal. For example, the image may comprise a map of at least a portion of the surface.

In any of the above embodiments, the system may include plural sensors, with the controller in communication with the sensors and evaluating the sensor signals from each of the sensors. For example, each of the sensors may be associated with a region of the surface where the map is segmented into plural zones. Each zone may correspond to and have an icon representing one region of the surface.

In any of the above embodiments, the controller may change one icon of the icons when the controller determines that the sensor signals associated with the one region indicate for the one region a change between the movement covering or not covering the cleaning target area.

In another embodiment, the system further includes a transmitter which is in communication with the controller for sending the output signal from the controller to a remote device.

In another embodiment, the system further includes a user interface. The user interface is in communication with the controller and configured to initiate the controller evaluating the sensor signals.

In any of the above, the system may further include a timer, with the controller determining the time spent by a person or apparatus cleaning the surface using the timer.

In yet another embodiment, the sensor comprises a camera.

In any of the above, the system further includes a cleaning apparatus, such as a vacuum cleaner, a washing device, with the sensor detecting the movement of the cleaning apparatus.

According to another embodiment, a method of providing cleaning assistance to a person includes sensing pressure applied by the person to a surface, comparing the applied pressure to a cleaning target values, and generating an output signal in response to the comparing.

In one embodiment, an output signal is generated that indicates whether the pressure is below, at, or above the cleaning target value.

In any of the above, the method includes generating an image of the surface being cleaned, and indicating at the image whether the pressure applied at the surface is below, at, or above the cleaning target value. For example, the indication includes generating a map of the surface and indicating through the use of colors whether the pressure applied at the surface is below, at, or above the cleaning target value.

Optionally, a map is generated with zones. Further colors are used to indicate whether the pressure applied at each zone is below, at, or above the cleaning target value.

In one embodiment, the system transmits the output signal to a remote device.

In yet another embodiment, a method of providing cleaning assistance includes sensing movement across a surface, comparing the movement to a cleaning target area, and generating an output signal in response to the comparing.

In one embodiment, the output signal indicates whether the movement covers or not covers the cleaning target area.

For example, an image of the surface being cleaned may be generated, which indicates whether the movement covers or not covers the cleaning target area.

In one embodiment, a map of the surface is generated and indicates through the use of colors whether the movement covers or not covers the cleaning target area. Further, the map may be generated with zones, which uses colors to indicate whether the movement covers or not covers the cleaning target area.

In any of the above, the signal may be communicated by the system to a remote location. For example, the remote location may be a hospital network or may be a network of third party, including for example the cloud.

Optionally, where there is a display, the display may be resident at the medical apparatus or may be remote from the medical apparatus but communicate with the computer either wirelessly or through wired connections. For example, the display may communicate with the computer through a network.

In each case, the medical apparatus may comprise a patient support, such as a hospital bed. The surface that is monitored may include the mattress, the side rails, the footboard, and or the headboard.

In some embodiments, a system includes a medical apparatus and a computer. The medical apparatus includes a least one feature that is in communication with the computer and monitored by the computer. The computer is also in communication with a display that allows a person to view the feature and the pressure applied thereto or the movement across the feature.

For example, the medical apparatus may comprise a patient support, such as a hospital bed, with the computer integrated into the patient support.

In some embodiments, the computer acts as a thin client for at least one network service, thereby enabling upgrades, modifications, improvements, and customizations of the one or more functions performed by the computer at the medical apparatus. The network service may provide information, algorithms, data processing, and/or other features for the medical apparatus that relate to such features as: monitoring pressure applied to one or more components of the medical apparatus or monitoring movement across one or more components of the medical apparatus to determine whether such pressure or movement indicates that the surface of the component has been wiped down, and hence cleaned.

According to one embodiment, a patient support apparatus is provided that includes a base, a frame supported on the base, a patient support surface, a plurality of force sensors, and a controller. The patient support surface is adapted to support a patient thereon, and the plurality of force sensors are adapted to output signals corresponding to downward forces exerted on a surface of the patient support apparatus. The controller is in communication with the force sensors and adapted to analyze the output signals to determine if the signals are indicative of an applied force associated with wiping the surface to indicate that the surface has been cleaned.

According to other aspects, the patient support apparatus includes a user interface in communication with the controller, wherein the controller provides an indication to a healthcare worker via the user interface when the controller determines that the signals are indicative of the surface being wiped.

In one aspect, the user interface may be configured to prompt the healthcare worker to confirm or reject that the surface has been cleaned.

In other aspects, the user interface may be configured to prompt the healthcare worker to indicate that the surface is going to be cleaned to initiate the controller monitoring the signal from the sensors for the purpose of managing the cleaning of the apparatus.

According to another embodiment, a patient support apparatus is provided that includes a base, a frame supported on the base, a patient support surface, a plurality of sensors, and a controller. The patient support surface is adapted to support a patient thereon, and the plurality of sensors are adapted to output signals corresponding to a wiping motion or threshold downward force exerted on a surface of the patient support apparatus. The controller also includes a timer. The controller is in communication with the plurality of sensors and adapted to analyze the output signals to determine if the wiping motion or downward forces have been applied for a chosen passage of time to indicate that the surface has been cleaned.

According to other aspects, the patient support apparatus includes a user interface in communication with the controller, which user interface may be configured to prompt the healthcare worker to indicate the bed is unoccupied and ready for cleaning.

An exit alert system can be coupled to the patient support apparatus and adapted to issue an alert if a patient on the patient support surface moves beyond a threshold amount while the exit alert system is armed. When included, the controller is adapted to automatically disable the exit alert system if the user indicates that the bed is unoccupied and ready for cleaning. Alternately, the exit alert system may be used to indicate that the bed is unoccupied and ready for cleaning.

According to another embodiment, a patient support apparatus is provided that includes a base, a frame supported on the base, a patient support surface, a plurality of sensors, and a controller. The patient support surface is adapted to support a patient thereon. The sensors are adapted to output signals corresponding to wiping motion or downward forces exerted on a surface of the patient support apparatus. The controller is in communication with the plurality of sensors and adapted to record the output signals from the plurality of sensors over time to determine a history of cleaning events with respect to the patient support surface.

According to other aspects, the patient support apparatus includes a user interface in communication with the controller, which user interface may be configured to prompt the healthcare worker to indicate when a cleaning event is initiated and when it is terminated.

The controller may be adapted to time stamp each cleaning event and to display a time corresponding to each cleaning event when prompting the healthcare worker to indicate when a cleaning event is initiated and when it is terminated.

In any of the above, the plurality of force sensors may be load cells integrated into the patient support apparatus. Alternately, the plurality of sensors may be optical sensors.

According to still another embodiment, a patient support apparatus is provided that includes a base, a frame, a patient support surface, a plurality of sensors, a display, and a controller. The plurality of sensors are adapted to output signals corresponding to when threshold downward forces are exerted on or when wiping motion occurs across a plurality of surfaces of the patient support apparatus. The controller is in communication with the plurality of sensors and the display, and the controller is adapted use the signals from the plurality of sensors to display when a surface of the plurality of surfaces has been subject to a threshold downward force or a wiping motion indicative of a cleaning process.

In one aspect, the controller is adapted use the signals from the plurality of sensors to display at the display when a surface of the plurality of surfaces has been not been subject to a threshold downward force or a wiping motion indicative of a cleaning process.

For example, the display may include icons representative of each of the surfaces. Each icon may have a first appearance when the controller determines its representative surface has been subject to a threshold downward force or a wiping motion indicative of a cleaning process and having a second appearance when the controller determines its representative surface has been not subject to a threshold downward force or a wiping motion indicative of a cleaning process.

In one aspect, the controller is adapted use the signals from the plurality of sensors to display at the display when a surface of the plurality of surfaces has been not been subject to a threshold downward force or a wiping motion indicative of a cleaning process.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and is capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

BRIEF DESCRIPTION OF THE DRAWINGS

FIG. 1 is a schematic view of a cleaning management system;

DETAILED DESCRIPTION OF THE EMBODIMENTS

Figure 2A:
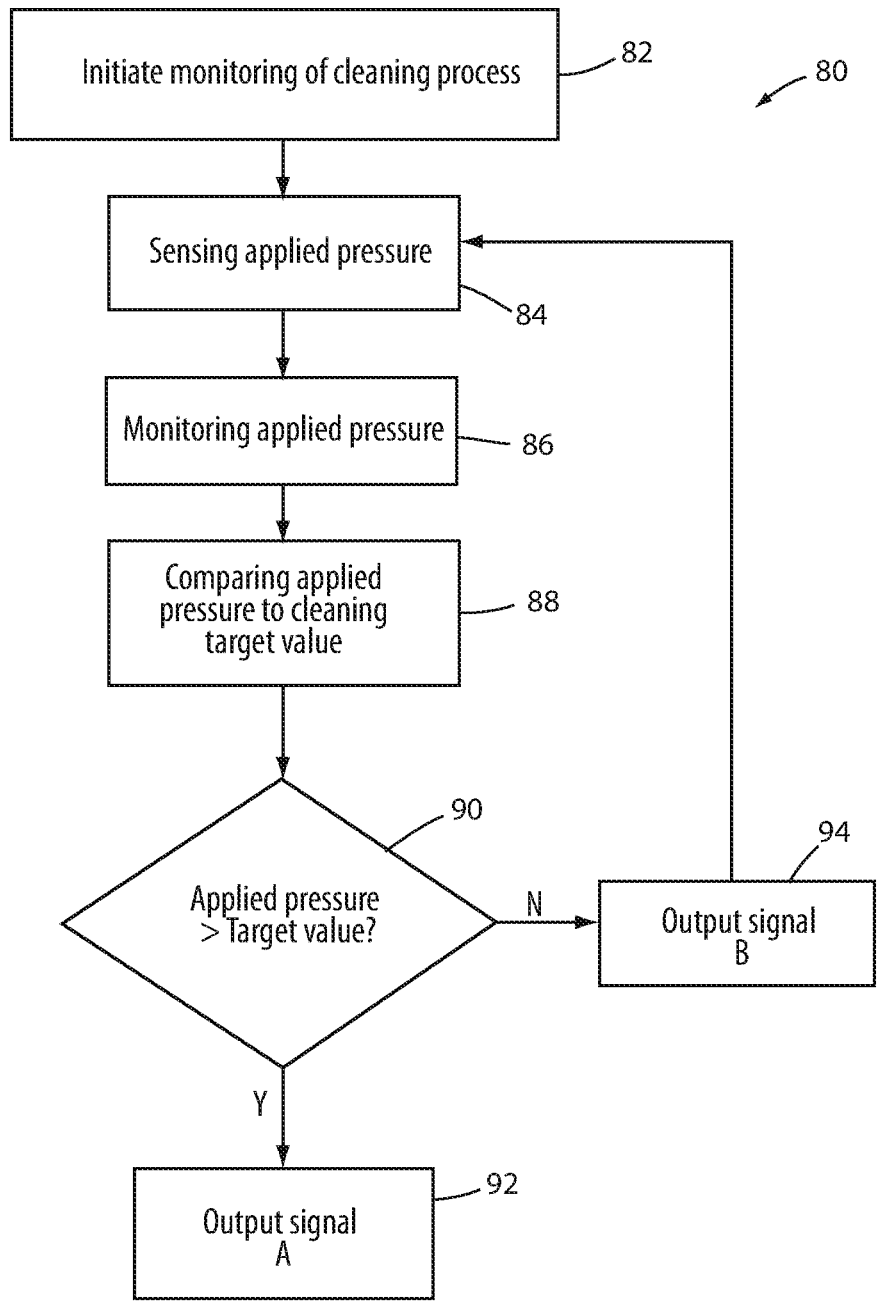
FIG. 2A is a flow chart of a software program that may be used in the control system of the cleaning management system.

Referring to FIG. 1, the numeral 10 generally designates a medical apparatus that includes a control system with electronics and an optional communication system for monitoring, training, providing feedback, and/or tracking the cleaning of medical apparatus 10. In the illustrated embodiment, medical apparatus 10 is a patient support apparatus, such as a stretcher, a cot, an intensive care bed, a med-surg bed, a maternity bed, or a medical recliner; however, it should be understood that apparatus 10 may comprise other medical apparatuses, such as an OR table or a treatment device, including a temperature management apparatus or the like.

Referring again to FIG. 1, patient support apparatus 10 includes a frame 16, a patient support surface or deck 18, a headboard 20, and a footboard 22. For example, frame 16 may include caster wheels 24 that can be selectively locked and unlocked so that, when unlocked, patient support apparatus 10 is able to be wheeled to different locations. Though not illustrated in the present embodiment, apparatus 10 may include elevation adjustment mechanisms adapted to raise and lower deck 18 with respect to casters 24. The elevation adjustment mechanisms may be hydraulic actuators, electric actuators, or any other suitable device for raising and lowering deck 18. In some embodiments, the elevation adjustment mechanisms may operate so that the orientation and/or configuration of deck 18 may also be adjusted.

Frame 16 supports deck 18, headboard 20, and footboard 22. Deck 18 in turn provides a surface on which a mattress 26, or other cushion, is positionable so that a patient may lie and/or sit thereon. Deck 18 may be made of a plurality of sections, some of which are pivotable about generally horizontal pivot axes. In addition, while not shown, patient support apparatus 10 may include side rails, including head side rails and foot side rails, which also may be movable between a raised position and a lowered position.

For examples of the construction of frame 16, deck 18, headboard 20, footboard 22, the elevation adjustment mechanisms, and/or the side rails reference is made to U.S. Pat. No. 7,690,059 issued to Lemire et al., and entitled HOSPITAL BED, the complete disclosure of which is incorporated herein by reference; or as disclosed in commonly assigned U.S. patent application Ser. No. 11/557,349, filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, issued on Apr. 8, 2014 as U.S. Pat. No. 8,689,376, the complete disclosure of which is also hereby incorporated herein by reference; or as embodied in the commercially available S3 bed sold by Stryker Corporation of Kalamazoo, Mich., and document in the Stryker Maintenance Manual for Stryker's MedSurg Bed, Model 3002 S3, (doc. 3006-109-002 Rev D), published in 2010, the complete disclosure of which is also hereby incorporated herein by reference. However, it should be understood that the construction of frame 16, deck 18, headboard 20, footboard 22, the elevation adjustment mechanisms, and/or the side rails may also take on other forms.

Referring again to FIG. 1, the numeral 50 generally designates a control system for patient support apparatus 10. As will be more fully described below, control system 50 is configured to monitor, track, provide feedback, and/or train a healthcare worker in the cleaning of medical apparatus 10. For example, control system 50 may be configured to monitor, track, provide feedback, and/or train a healthcare worker when cleaning one or more surfaces of apparatus 10. Such surfaces may include the side rails, headboard 20, footboard 22, mattress 26, or mattress sensing mat 26a. Control system 50 may have a software application, such as shown in FIG. 2A, 2B, 3A, or 3B, which monitors the cleaning process and which may provide feedback to the healthcare worker who is cleaning the surface in the form of images, icons, sounds, lights, etc., that indicate whether the cleaning process achieved a target value or a target area has been cleaned based on either applied pressure or displacement on or motion of the healthcare worker over the surface to be cleaned.

Further, the software application may time stamp the cleaning process to create a log of the date and time when the cleaning process occurred. The target values or target areas are stored in the memory of the control system. It should be understood that the standards or protocols for the target values or target areas may vary by patient; therefore, control system 50 may have several target values or target areas stored therein (and they may be selectable by a healthcare provider either locally at the apparatus or remotely from a nurse call station, for example) and further may receive updates from time to time when needed or requested.

In addition, control system 50 may send a notification to a remote device, such as a nurse call station or the health facility network (more fully described below), of when the cleaning process was competed and optionally, as noted below, in the event that the cleaning process is halted but was not completed to the standards or protocols saved in the memory 54 of the control system. Further, control system 50 may send information, such as logged information, to the remote device for tracking and optionally for analysis. In this manner, control system 50 will allow a healthcare facility to monitor the cleaning process for one or more apparatuses and to determine when the last time an apparatus was cleaned.

As best seen in FIG. 1, control system 50 includes a computer or controller 52 and a memory 54 in communication with the controller 52. In addition, control system 50 includes a user interface 56, at least one device interface 58, at least one transceiver 60, and sensors, for example, sensors 42 for detecting the pressure on one or more surfaces on patient support apparatus 10. The components of control system 50 communicate with each other using conventional electronic communication techniques. In one embodiment, controller 52 communicates with memory 54, user interface 56, and sensors 42 using I-squared-C communications. Other types of serial or parallel communication can alternatively be used. In some other embodiments, different methods may be used for different components. For example, in one embodiment, controller 52 communicates with user interface 56 via a Controller Area Network (CAN) or local Interconnect Network (LIN), while it communicates with memory 54, and sensors 42 using I squared C. Still other variations are possible.

User interface 56 may include a plurality of user actuatable interfaces 64, such buttons or the like, that a healthcare worker can press in order to control various features of the patient support apparatus, including initiating the cleaning process monitoring system. For example, one of the interfaces 64 may generate a signal to the control system that the bed is unoccupied and ready for cleaning. Another interface may be used by a user to signal to the control system that the healthcare worker is going to start cleaning apparatus 10. And, another interface may allow a healthcare worker to select a surface to be cleaned. Yet another interface may be pressed by healthcare worker to indicate that they have finished cleaning the selected surface. Optionally, these signals may be generated and input in to control system 50 using a voice activation system or by a remote device, such as a hand held user actuatable device or a nurse call station.

User interface 56 may include a display 66 integrated therein. Display 66 may comprise a touchscreen display with a graphical interface capable of displaying text and/or graphics and sensing the location that a user's finger touches the display. Although it will be understood that display 66 could be modified to be a normal LCD display without touchscreen capabilities that used hard or soft buttons to interact therewith, or still other types of displays. Display 66 is configured to show a display of the surface being cleaned, and the display could change to show that the cleaning process has met a stored standard or protocol. For example, display 66, may be configured to provide a menu with touch selectable buttons (which can form user actuatable interfaces 64 or provide additional user actuatable interfaces) for selecting functions associated with the cleaning process. The touch selectable buttons may include, as noted above buttons, for starting and indicating completeness of the cleaning.

In one embodiment, display 66 may have an image, such as a graphical image, of the apparatus, which is segmented into regions that correspond to the surfaces that can be monitored. When selected, the regions can indicate when they are selected and when the region has been cleaned successfully or not. For example, the regions may provide a visual indication in the form of a color to indicate when they are selected and when the region has been cleaned successfully or not. As the surface is cleaned, the color may change, for example when the cleaning process has met one or more standards, including intermediate standards. In addition, control system 50 may generate other alerts, such as audible or other visual alerts, such as by a light.

By providing visual or audible indications of whether the surface is cleaned or not, control system 50 can provide feedback to the healthcare worker. The feedback may be provided as the healthcare worker cleans in real time or in time increments. For example, if a region is not properly cleaned, the healthcare worker may be given an alert signal. For example, if the cleaning process appears to have halted but the cleaning process does not meet the standard, the alert can inform the healthcare worker that they need to go back to the region to complete the process until they are given an indication that the region has been cleaned to the stored standard. Thus, system 50 may be used to train healthcare workers to improve their cleaning techniques. Thus, control system, 50 may also provide a teach mode of operation.

In addition, control system 50 may be configured in one embodiment to highlight a zone on the image at display 66 to tell a healthcare worker where to start cleaning and then as the area that corresponds to the zone is cleaned, change the highlight to another color and then highlight another zone to instruct the healthcare worker to move to the next area for cleaning. This process can be repeated until all surfaces are cleaned.

Controller 52 includes one or more microcontrollers, microprocessors, and/or other programmable electronics that are programmed to carry out the functions described herein. It will be understood that controller 52 may also include other electronic components that are programmed to carry out the functions described herein, or that support the microcontrollers, microprocessors, and/or other electronics. The other electronic components include, but are not limited to, one or more field programmable gate arrays, systems on a chip, volatile or nonvolatile memory, discrete circuitry, integrated circuits, application specific integrated circuits (ASICs) and/or other hardware, software, or firmware, as would be known to one of ordinary skill in the art. Such components can be physically configured in any suitable manner, such as by mounting them to one or more circuit boards, or arranging them in other manners, whether combined into a single unit or distributed across multiple units. Such components may be physically distributed in different positions on patient support apparatus 10, or they may reside in a common location on patient support apparatus 10. When physically distributed, the components may communicate using any suitable serial or parallel communication protocol, such as, but not limited to, CAN, LIN, Firewire, I-squared-C, RS-232, RS-485, etc.

Sensors 42 are, in some embodiments, conventional load cells, or similar force measuring sensors, that are positioned to detect the amount of downward force exerted by a healthcare worker on the side rails, headboard, footboard or mattress. In some embodiments, the force sensors 42 may be configured so that, in addition to downward forces, they are also able to detect forces exerted in generally horizontal directions (both laterally and longitudinally). Further, sensors 42 may detect how vigorously the surface is being cleaned. For example, sensors 42 may detect a change in amplitude, frequency, and duration of the force applied to the surface, which can be used by algorithms resident in controller 52 and/or memory 54 to determine the extent of the cleaning process. Alternately, sensors 42 may comprise accelerometers that detect displacement.

For example, when detecting pressure on a mattress, the load cells may be located between a load frame positioned between the deck and the frame. In the case of the side rails, headboard and footboard, the load cells may be located beneath the skin of the side rail, headboard and footboard. For example, the side rails, headboard and footboard may be each formed from a tubular frame which is then covered by a thin shell (skin) of a polymer material. In which case, the load cells may be positioned in the respective side rail, headboard and footboard, just beneath the polymer shell or skin. Alternately, sensors 42, whether pressure sensing sensors or accelerometers, may be located near or at the surface of a component.

Controller 52 may be in direct communication or in communication through interface 58 with each of sensors 42 on the side rails, headboard, or footboard to receive the outputs from each sensor 42. Interface 58 may be configured to communicate with sensors 42 in mattress 26 either though a wireless or wired connection. Mattress 26 may be a mattress of the type disclosed in commonly assigned U.S. patent application Ser. No. 13/836,813, filed Mar. 15, 2013, and Ser. No. 14/308,131, filed Jun. 18, 2014, entitled INFLATABLE MATTRESS AND CONTROL METHODS (STR03A P-400A) and PATIENT SUPPORT (STR03A P-405B), respectively, the complete disclosures of both of which are hereby incorporated herein by reference. Such mattresses include a plurality of inflatable bladders whose inflation pressure is controllable by one or more controllers contained with the mattress. The mattress may further include a plurality of sensors used for detecting information about the status of the mattress, such as, but not limited to, one or more depth sensors, fluid pressure sensors, temperature sensors, patient interface pressures sensors, and/or humidity sensors, or may be used to detect information about the patient, such as vital signs, temperature or activity.

In addition, interface 58 may be in communication with a mattress accessory 26a, such as a mattress pressure sensing mat or pad, which may form part of mattress 26 or may be separate components. Such pressure sensing mats are used to detect the interface pressures between the patient and the support surface the patient is positioned on, and can be useful for monitoring pressures so as to avoid the development, or potential development, of bed sores. In the present embodiment, such pressure sensing mats can be used to detect the pressure applied by a healthcare worker when cleaning the mattress. A suitable flexible pressure sensing mat is of the type disclosed in commonly assigned PCT patent application serial number PCT/US12/27402, filed Mar. 2, 2012 by Stryker Corporation, and entitled SENSING SYSTEM FOR PATIENT SUPPORTS, the complete disclosure of which is hereby incorporated herein by reference. Such a flexible pressure sensing mat may forward pressure information, including but not limited to, a pressure distribution map, to controller 52, for then display at display 66.

In some embodiments, interface 58 is a Controller Area Network connection that communicates with sensors 42 and mattress accessories 26a, while in other embodiments, interface 58 takes on other forms. In one embodiment, interface 58 is a wireless connection, such as that disclosed in commonly assigned U.S. patent application Ser. No. 13/296,656, filed by applicants Guy Lemire et al. and entitled PATIENT SUPPORT WITH WIRELESS DATA AND/OR ENERGY TRANSFER, issued on Oct. 21, 2014 as U.S. Pat. No. 8,864,205, the complete disclosure of which is hereby incorporated herein by reference.

In still other embodiments, control system 50 may include more than one interface 58. Each interface 58 may be of the same or different type (e.g. some may be wired, some may be wireless, or they both may be wired or wireless but use different communication protocols). In one embodiment, a control system 50 includes a near field communications transceiver that communicates in any of the manners, and with any of the devices, disclosed in commonly assigned U.S. patent application Ser. No. 13/802,992, filed Mar. 14, 2013 by applicants Michael Hayes et al, and entitled COMMUNICATION SYSTEMS FOR PATIENT SUPPORT APPARATUSES (STR03 R&D P-397A), the complete disclosure of which is hereby incorporated herein by reference. Such a near field communications transceiver can be used for establishing associations between apparatus 10 and a healthcare worker, for example, who is wearing a near field ID tag, such as an RF ID tag, to track who was cleaning apparatus 10 and also the amount of time the healthcare worker was in close proximity to apparatus 10 during a cleaning cycle. This information may also be transmitted to the remote device as noted above.

As noted above, control system 50 is configured to monitor, track, provide feedback, and/or train a healthcare work in the cleaning of medical apparatus 10. For example, referring to FIG. 2A, control system 50 may have a cleaning monitoring software application 80. Application 80 can be a thin client application, a fat client application, or a local application. Thin client applications can communicate with one or more network services, which are available on one or more remote networks, such as a healthcare facility network and/or the Internet. The term "thin client" as used herein shall be given its ordinary and accustomed meaning in the field of computer science and software. In general, a thin client refers to a computer or computer program which depends substantially on another computer or, in this case, one or more network services, to fulfill its programmed computational functions. In some embodiments, controller 52 may be configured to support both fat and thin client applications, as well as applications that are purely local.

Referring again to FIG. 2A, application 80 begins with initiating the monitoring of the cleaning process at 82, for example, by a user, such as healthcare worker, by pressing a user actuatable interface 64, such as start icon or button, at user interface 56. After the user initiates the monitoring process, controller 52 monitors the signals from sensors 42 of the target surface being cleaned, which sense the pressure 84 or displacement being applied to the target surface. For example, as noted above support apparatus 10 may have multiple surfaces that can be monitored during cleaning. Part of the initiating step may include a selection, for example, from a menu or an icon with touch selectable areas that can designate what surface of the apparatus is going to be cleaned. Controller 52 monitor the sensors 42 to monitor the applied pressure 86 (e.g. at the selected surface) or displacement and then compares the applied pressure to a target value at 88. If controller 52 determines that the applied pressure or displacement is greater than or equal to the target value, controller 52 will generate an output signal 92. For example, the signal may indicate that the cleaning is acceptable and further may be stopped. If controller 52 determines that the applied pressure or displacement is less than the target value, controller 52 will generate another signal 94 and then continue monitoring. Signal 94 may indicate that the cleaning is unacceptable. For example, this signal may actuate a light, or cause the controller to generate a sound. Further, display 66 may be responsive to either signal, for example, by generating an image or icon, including a dynamic image or icon, that indicates whether the cleaning process met the standard or not.

For example, display 66 may have an image or icon that represents the apparatus, which may be divided into segments representing the surfaces that can be monitored. A suitable image or icon may be a map of the apparatus, or at least a portion of the apparatus, which may be zoned to indicate different regions or areas of the surface being cleaned. The signals then may be used to highlight the zone of the map that corresponds to the area that has been cleaned and indicate through a color whether or not the target surface has been adequately cleaned. For example, when the monitoring process is initiated the image that corresponds to the target surface may be highlighted with one color, for example, red, and then when the area is cleaned to the standards set by the target value, the controller 52 will change the color of the image to another color, such as green. Intermediate colors may be used, for example, when intermediate target values are reached. Similarly, the image or icon may be accompanied by another indicator, as noted above, such as an audible sound, which also may be used to indicate to the healthcare worker that the target area is cleaned or not. Alternately or in addition, a signal may be transmitted remotely from the apparatus.

Figure 2B:
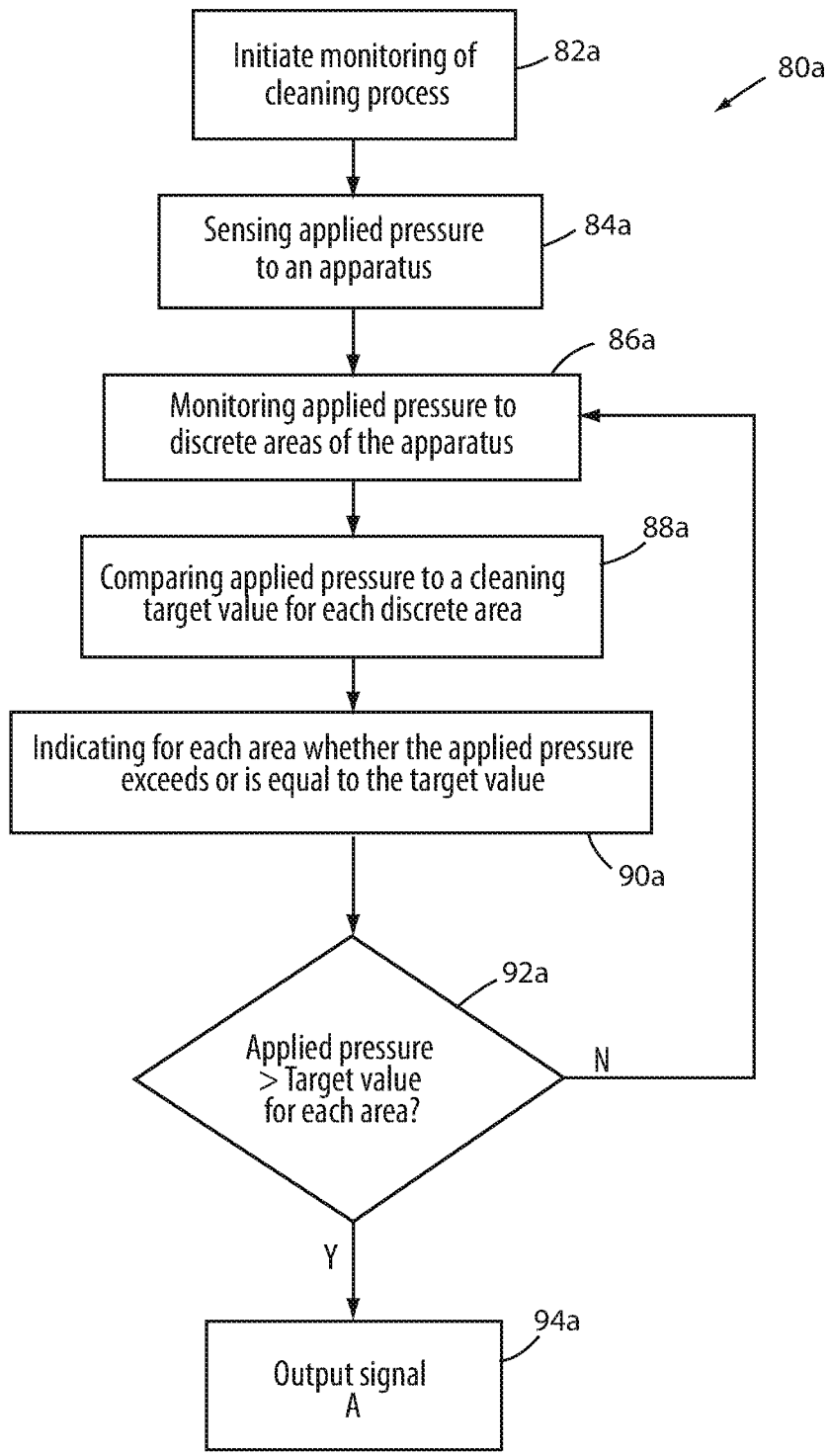
FIG. 2B is a flow chart of a second embodiment of the software program that may be used in the control system of the cleaning management system.

In another embodiment, as shown in FIG. 2B, application 80*a* begins with initiating the monitoring of the cleaning process at 82*a*, for example, by a user, such as healthcare worker, by pressing a user actuatable interface 64, such as start icon or button, at user interface 56. As noted above support apparatus 10 may have multiple surfaces that can be monitored during cleaning. Part of the initiating step may include a selection, for example, from a menu or an icon with touch selectable areas to designate what surface of the apparatus is going to be cleaned. Further, each selected surface may have multiple sensors so that discrete regions or areas of the target surface may be monitored.

After the user initiates the monitoring process, controller 52 monitors the signals from sensors 42 of the selected surface being cleaned, which sense the pressure 84*a* or displacement being applied to the discrete areas. Controller 52 monitor the sensors 42 to monitor the applied pressure 86*a* or displacement at the discrete areas and then compares the applied pressure to a target value for each discrete area at 88*a*. Controller 52 can then display an indication for each area whether the applied pressure or displacement for each discrete area is greater than or equal to the target value for each discrete area. If the applied pressure or displacement is greater than or equal to the target value, the controller may also generate a signal 92*a*. For example, the signal may indicate that the cleaning is acceptable and further may be stopped. If controller 52 determines that the applied pressure or displacement is less than the target value for any discrete area, controller 52 will continue to monitor the pressure or displacement until the applied pressure or displacement to all discrete areas are equal to or are greater than the target value, at which time controller 52 will output a signal 94*a*. As noted above, this signal may actuate a light or cause the controller to generate a sound.

Alternately or in addition, display 66 may be responsive to the signals. For example, display 66 may generate a display that represents the apparatus, which may be divided into segments representing the surfaces that can be monitored. Each segment of the display may be divided into zones that correspond to discrete areas of the surface. In response to the signal, controller 52 may indicate what surface is being cleaned when it has been cleaned, for example, through a color. Further, controller 52 may indicate by the zones whether the target surface has been adequately cleaned. In other words, controller 52 can generate an image corresponding to the surfaces, which are capable of being monitored, segmented into zones that represent the discrete areas with each zone having an indication of whether the discrete area has been cleaned.

For example, when the monitoring process is initiated, the image may be highlighted with one color, for example, red, and then when one of the discrete areas is cleaned to the standards set by the target value, the controller 52 will change the color of the image to another color, such as green. Intermediate colors may be used, for example, when intermediate target values are reached. Similarly, audible sounds may be used in conjunction with the display to indicate to the healthcare worker that the target area is cleaned or not.

According to yet another embodiment, sensors 42 may detect electromagnetic radiation or signals, for example, from a wearable device 70, such as a near field transmitter, including an RF ID tag worn by a healthcare worker. Thus, in one embodiment, apparatus 10 includes wireless circuitry built into it that communicates with the RF ID tags, or other tags, worn by the healthcare worker. Such communication enables controller 52 to know when a healthcare worker is positioned within the vicinity of apparatus 10 and, further, where their hand is (assuming that the RF ID tag is on the arm that is cleaning the apparatus) and where it moves relative to the sensor or sensors. Thus instead of detecting pressure, sensors 42 may be configured to detect motion. Therefore, rather than comparing the signals to a target value of pressure, the controller uses a target area as the standard. Further, when the healthcare worker leaves the vicinity of apparatus 10—as detected by the RF ID tag communication circuitry—patient support apparatus 10 may be configured to automatically shut off the monitoring system. Similarly, by sensing the healthcare worker near the apparatus, for example, when the apparatus is known not to be occupied as noted below, control system 50 may automatically initiate the monitoring system. For suitable software applications for implementing the monitoring system, reference is made to the description of FIGS. 3A and 3B below.

Control system 50 and wearable device 70 may communicate with each other via near field communications, such as disclosed in commonly assigned U.S. patent application Ser. No. 13/802,992, filed Mar. 14, 2013, by applicants Michael Hayes et al., and entitled COMMUNICATION SYSTEMS FOR PATIENT SUPPORT APPARATUSES (STR03 R&D P-397A), the complete disclosure of which is hereby incorporated herein by reference. Because near field communication has only a short communication range, the fact that apparatus 10 is able to communicate with a device worn by a user—such as a near field tag—is interpreted by apparatus 10 to mean that the healthcare worker is near apparatus 10, and when combined with the readings from sensors 42 indicate that the hand or arm of the healthcare worker is moving across the target surface and that apparatus 10 is being cleaned.

Figure 3A:
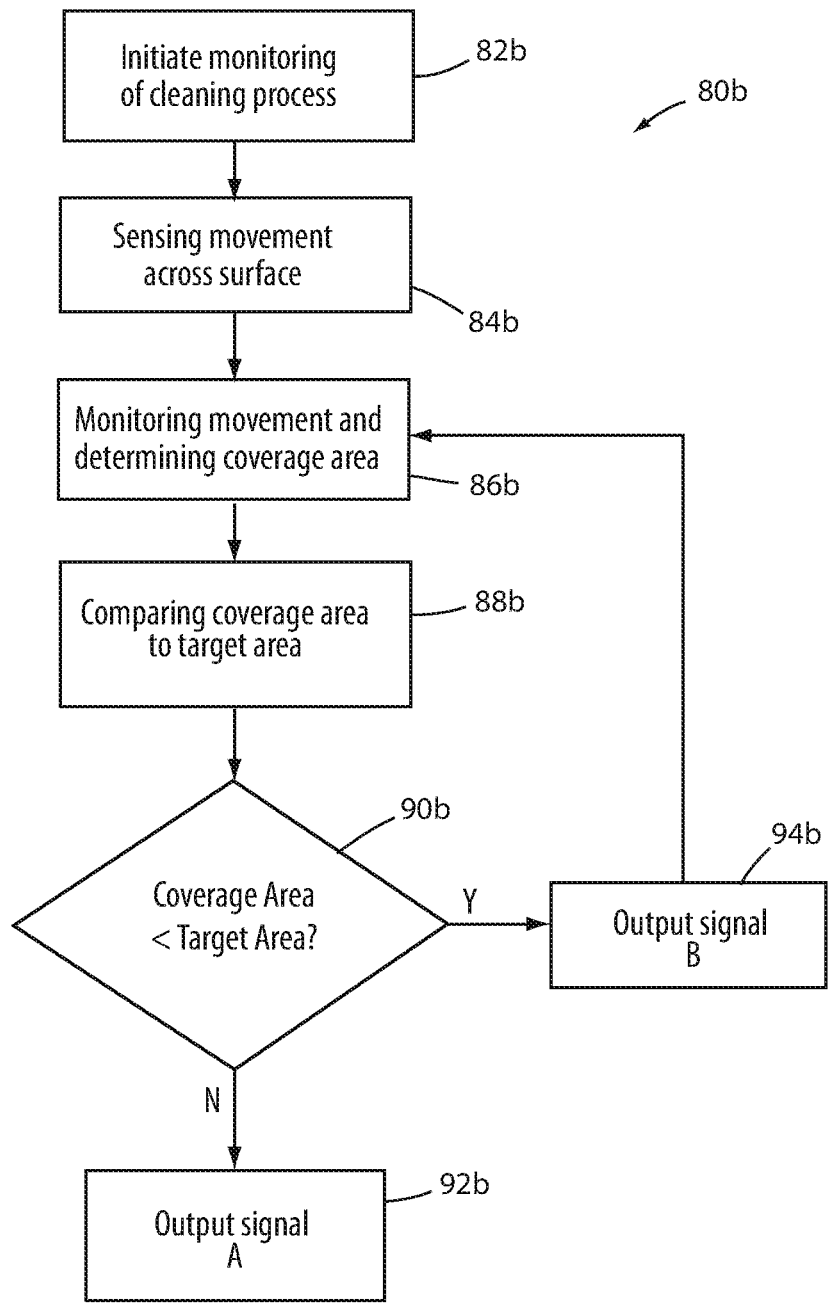
FIG. 3A is a flow chart of a third embodiment of the software program that may be used in the control system of the cleaning management system.

In yet another embodiment, referring to FIG. 3A, control system, 50 may include a software application that enables monitoring of the cleaning of apparatus 10 using a camera 90, such as a motion sensing camera of the type sold under the brand name Kinect™, by Microsoft Corp. of Redmond, Wash. Camera 90 can be used to recognize a surface of the apparatus (based on images stored in the camera) and then recognize when an object passes over the image. Camera 90 is in communication with control system 50 and can therefore be used to detect movement of an object, for example, the healthcare worker's hand, across a defined surface. As noted above, the healthcare worker may select which surface is going to be cleaned. Once the surface is selected, control system 50 will communicate with camera 90 which surface is to be sensed by the camera. Controller 52 will analyze the signals from camera 90 to see if the entire surface of the selected surface has been covered by the motion of the healthcare worker or not.

For example, referring to FIG. 3A, a software application 80*b* is initiated, for example, when a user initiates the monitoring of the cleaning process at 82*b*. Movement across the surface is sensed at 84*b* by camera 90. Controller 52 receives the signals from camera 90 and analyzes the signals from camera 90 to monitor the movement and further determine the area wiped or covered ("coverage area") by the healthcare worker at 86*b*. Controller 52 compares the coverage area to a target area (e.g. the selected surface) at 88*b* and then determines at 90*b* whether or not the coverage area is less than the target area. The controller 52 determines that the coverage area is less than the target area, controller 52 will generate a first signal at 94*b* and then continues monitoring the movement of the healthcare worker across the surface until such time that the coverage area is equal to the target area. If the coverage area is equal to the target area, then controller 52 will output a second signal at 92*b* and further stop the monitoring process. For examples of suitable signals or displays reference is made to the above. A similar process may be used based on the input of the sensors described above.

Figure 3B:
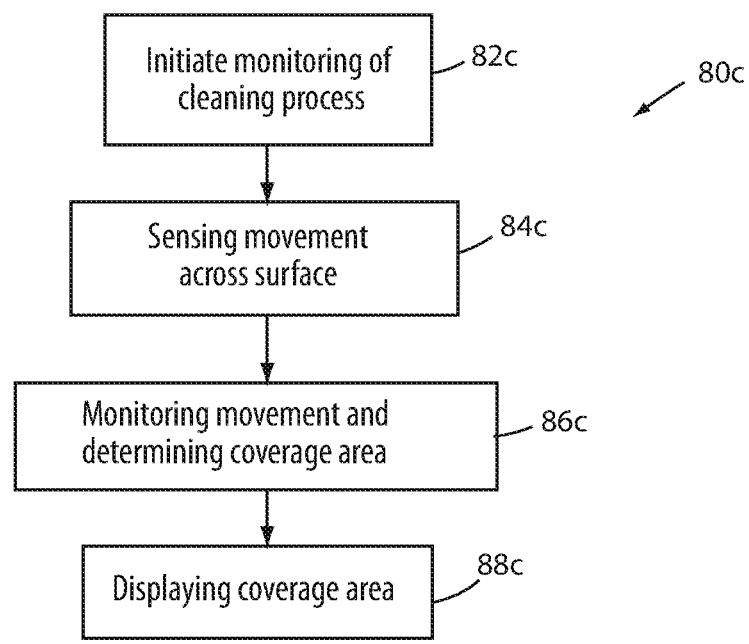
FIG. 3B is a flow chart of a fourth embodiment of the software program that may be used in the control system of the cleaning management system.

Referring to FIG. 3B, the numeral 80*c* designates yet another embodiment of a software application that may be used by control system 50. Application 80*c* starts with the initiation of the monitoring of the cleaning process at 82*c*, for example, as initiated by a healthcare worker. Movement across the surface to be cleaned is sensed at 84*c*, for example, by camera 90 or by sensors 42 (in response to detecting movement of a near field transmitter, as noted above). Controller 52 monitors the movement across the surface and determines the area covered ("coverage area") at 86*c*. Controller 52 evaluates the signals from camera 90 or sensors 42 to determine the area of coverage using algorithms stored in memory 54. Further, controller 52 then displays the coverage area at 88*c*.

For example, as described above, display 66 may include an image or icon that represents the apparatus and, further, may be segmented to designate (through color, etc.) the surfaces that can be monitored during cleaning. When a surface is selected, the segment of the image that corresponds to the selected surface may be indicated as being monitored. Further, the segment may be zoned to correspond to discrete regions or areas of the selected surface. As the selected surface is cleaned, the areas may change to indicate the surface has been effectively cleaned. For example, the areas may be color coded, with one color indicating that the area of the surface has not yet been cleaned, with another color indicating that the area of the surface has been cleaned, similar to the map as noted above.

In one embodiment, as noted, the target areas may include a surface on the mattress, side rails, headboard or footboard. Further, the target area may be a segment of the component. For example, for the side rails, headboard or footboard, the target area may be the top section of the side rail, headboard, or footboard.

In yet another embodiment, the signal(s) that is generated when the cleaning has not been found to be acceptable may be sent a remote location, such as a nurse call station or a healthcare facility network to alert someone other than the healthcare worker that the apparatus has not been properly cleaned.

In yet another embodiment, data or information about the cleaning process may be forwarded by the application to a network service that stores the data to allow logging of and/or studies of the data. The types of studies are customizable according to the interests of the healthcare facility and/or third party, or according to the interests of a group of healthcare facilities. Such studies might include, for example: correlations between the cleaning process and clinical outcomes; housekeeping procedure studies; or infection control studies. By finding patterns, it may be possible to design a cleaning system that is more efficient and effective.

The thin client, fat client, and/or local applications may be used to enable the use of the various features described above, including the detecting and/or tracking of the cleaning process, and/or the tracking or monitoring of associations. For more details of suitable thin client applications and fat client applications, and a suitable communication layout reference, is made to U.S. patent application Ser. No. 14/211,613, entitled PATIENT SUPPORT APPARATUS WITH REMOTE COMMUNICATIONS, filed on Mar. 14, 2014 (STR03 R&D P414B), which is incorporated by reference herein in its entirety.

In some embodiments, the communications link between controller 52 and the remote devices may be a wired communications link, such a wired connection may be carried out by an Ethernet cable, a serial cable, or by other cables. In still other embodiments, a communications link may be a wireless link that, in some instances, is carried out through the use of one or more mesh networks that patient support apparatuses 10 are part of. Such use of mesh networks to communicate information from patient support apparatuses 10 to a healthcare network, such as a network, are disclosed in commonly assigned U.S. patent application Ser. No. 13/802,855 filed Mar. 14, 2013 by applicants Michael Hayes et al. and entitled PATIENT SUPPORT APPARATUS COMMUNICATION SYSTEMS, and commonly assigned U.S. patent application Ser. No. 13/483,683 filed by Becker et al. and entitled COMMUNICATION SYSTEM FOR PATIENT HANDLING DEVICES, issued on Jun. 11, 2013 as U.S. Pat. No. 8,461,982, the complete disclosures of both of which are hereby incorporated herein in their entirety by reference. Another type of software application that may be resident (or downloaded) on control system 50 may monitor the length of time that a healthcare worker is present during the cleaning process for billing purposes. By keeping track of the amounts of time a healthcare worker is present during the cleaning process, a healthcare facility can use that information to generate invoices that are more reflective of the actual amount of medical resources used by a particular patient. Further, such software applications may be configured to automatically transmit their accumulated usage information to a remote server that uses such information to generate invoices to the healthcare facility and/or for the purpose of studying the use of a cleaning process.

One type of software application that may be resident on controller 50 (or uploaded) includes a manufacturer software application. The software application may allow a medical apparatus, such a patient support apparatus 10, to communicate data directly with one or more other medical apparatuses 10. Another type of software application may include a healthcare facility application, which can be used to perform assessments (e.g. efficacy of the cleaning protocol standards, etc.) and/or to test other cleaning protocols.

It will also be understood by those skilled in the art that, although FIG. 1 only depicts a single patient support apparatus 10, multiple patient support apparatuses 10 will typically be in communication with the various network services, and as such each can provide input to the information and data gathered to better assess the efficacy of any given cleaning protocol.

Figure 4:
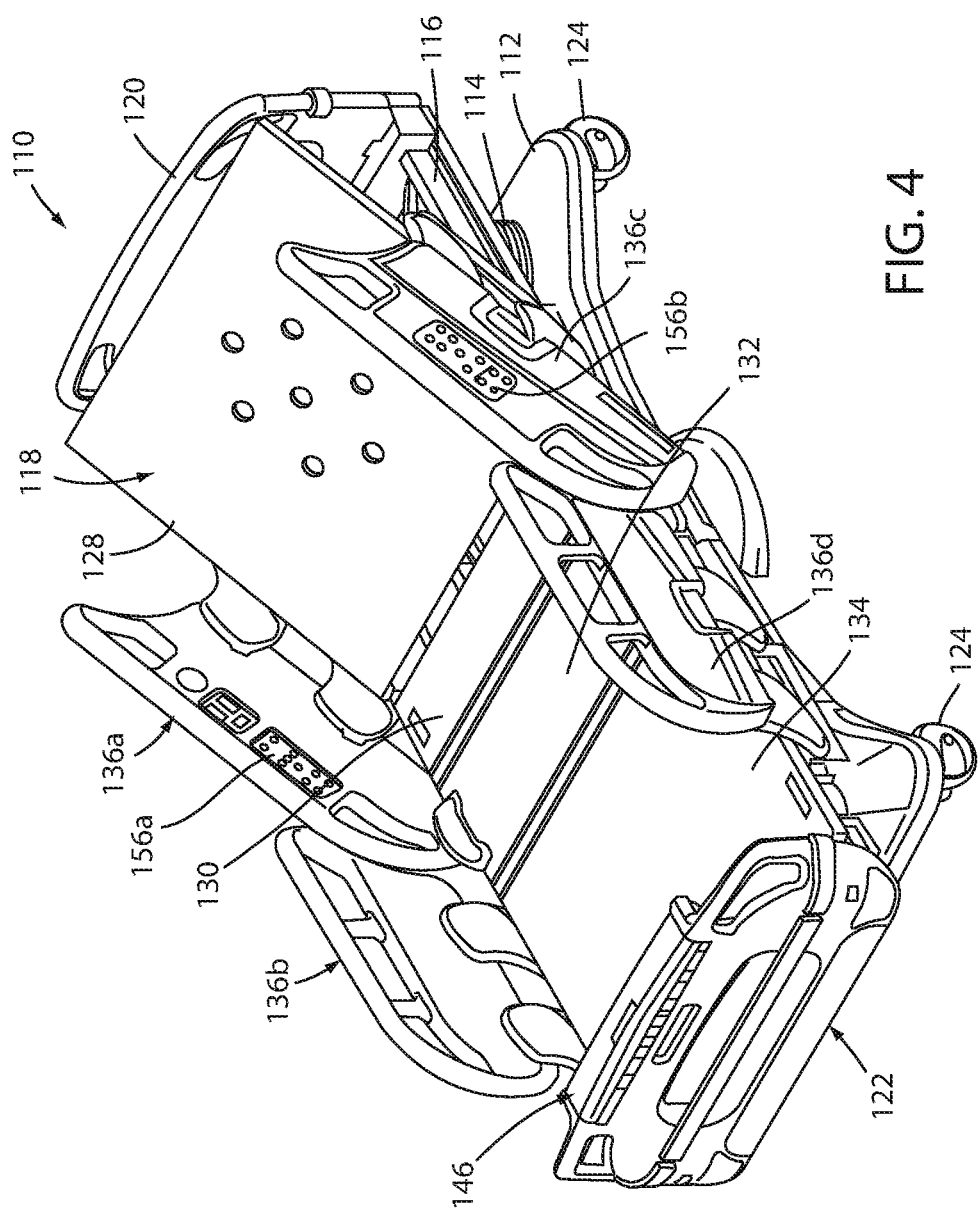
FIG. 4 is a perspective view of a medical apparatus in the form of a hospital bed that incorporates the cleaning management system.

Referring to FIG. 4, another embodiment of a medical apparatus 110, in the form of a hospital bed patient support apparatus, is illustrated. Although shown as a hospital bed, it should be understood that the cleaning monitoring system described hereon may be incorporated into other patient support apparatuses, such as a stretcher, a cot, a medical chair, a temperature management device, and other medical equipment and devices.

In the illustrated embodiment, apparatus 110 includes a base 112, a pair of elevation adjustment mechanisms 114, a frame or litter assembly 116, a patient support surface or deck 118, a headboard 120, and a footboard 122. For example, base 122 may include caster wheels 124 that can be selectively locked and unlocked so that, when unlocked, patient support apparatus 110 is able to be wheeled to different locations. Elevation adjustment mechanisms 114 are adapted to raise and lower frame 116 with respect to base 112. Elevation adjustment mechanisms 114 may be hydraulic actuators, electric actuators, or any other suitable device for raising and lowering frame 116 with respect to base 112. In some embodiments, elevation adjustment mechanisms 114 operate independently so that the orientation of frame 16 with respect to base 112 may also be adjusted.

Frame 116 may provide a structure for supporting patient support surface 118, headboard 120, and footboard 122. Patient support surface 118 provides a surface on which a mattress 126, or other cushion, is positionable so that a patient may lie and/or sit thereon. Patient support surface 118 may be made of a plurality of sections, some of which are pivotable about generally horizontal pivot axes. In the illustrated embodiment shown in FIG. 4, patient support surface 118 includes a head section 128, a seat section 130, a thigh section 132, and a foot section 134. Head section 128, which is also sometimes referred to as a Fowler section, is pivotable between a generally horizontal orientation (not shown in FIG. 4) and a plurality of raised positions (one of which is shown in FIG. 4). Thigh section 132 and foot section 134 may also be pivotable in some embodiments. In addition, patient support apparatus 110 may include four side rails: a right head side rail 136a, a right foot side rail 136b, a left head side rail 136c and a left foot side rail 136d (not shown). Side rails 136 are movable between a raised position (such as configuration shown in FIG. 4) and a lowered position.

For examples of the construction of base 112, elevation adjustment mechanisms 114, frame 116, patient support surface 48, headboard 120, footboard 122, and/or side rails 136 reference is made to U.S. patent application Ser. No. 11/612,428, filed by Lemire et al., and entitled HOSPITAL BED, issued on Apr. 6, 2010 as U.S. Pat. No. 7,690,059, the complete disclosure of which is incorporated herein by reference; or as disclosed in commonly assigned U.S. patent application Ser. No. 11/557,349, filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, issued on Apr. 8, 2014 as U.S. Pat. No. 8,689,376, the complete disclosure of which is also hereby incorporated herein by reference; or as embodied in the commercially available S3 bed sold by Stryker Corporation of Kalamazoo, Mich., and document in the Stryker Maintenance Manual for Stryker's MedSurg Bed, Model 3002 S3, (doc. 3006-109-002 Rev D), published in 2010, the complete disclosure of which is also hereby incorporated herein by reference. However, it should be understood that the construction of base 112, elevation adjustment mechanisms 114, frame 116, patient support surface 118, headboard 120, footboard 122 and/or side rails 136 may also take on forms different from what is disclosed in these documents.

Figure 5:
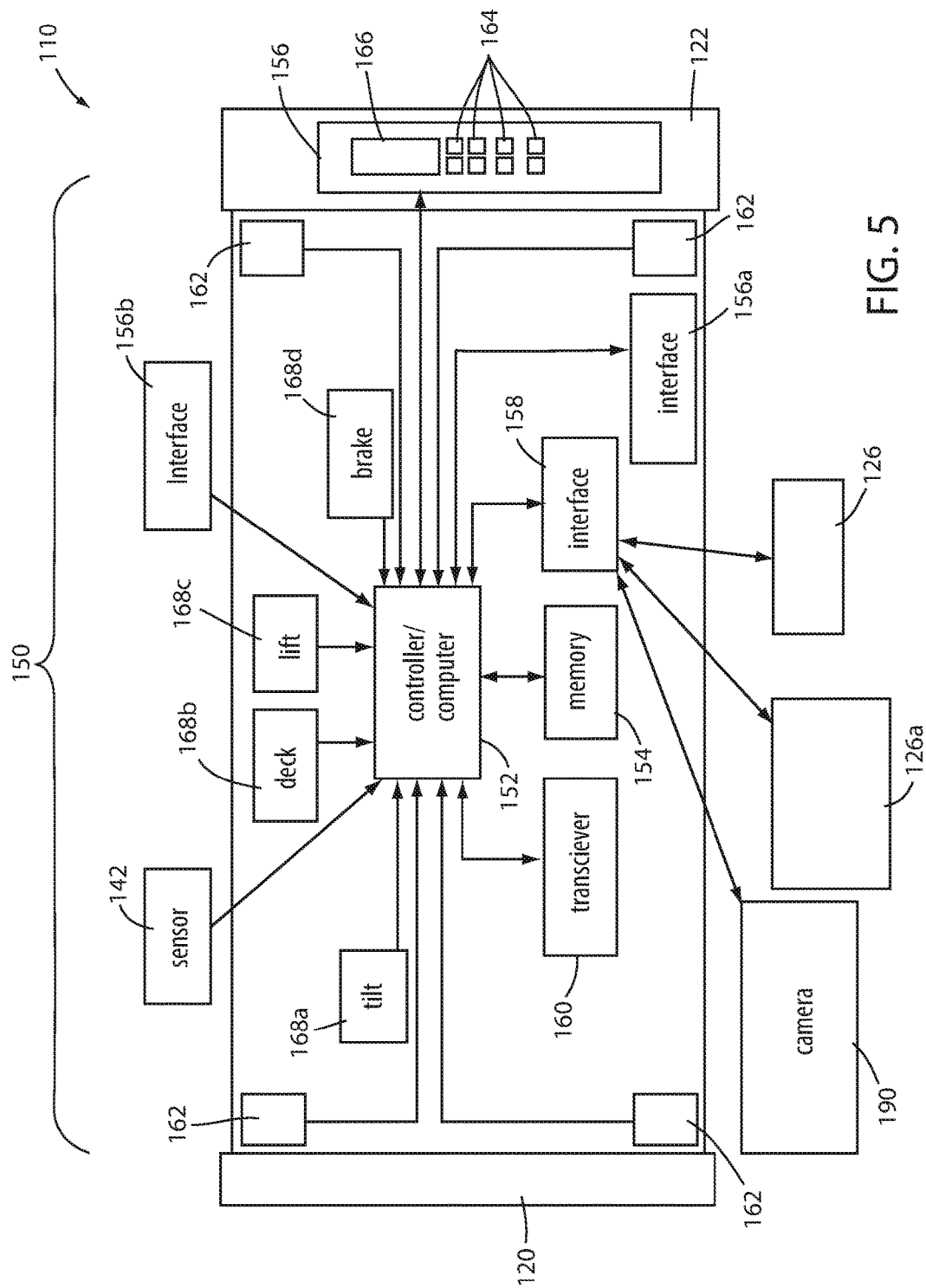
FIG. 5 is a diagram of illustrative layout of the control system of the medical apparatus of FIG. 4.

Referring to FIG. 5, the numeral 150 generally designates a control system for patient support apparatus 110. Similar to control system 50, described above, control system 150 is configured to sense pressure applied to selected surfaces of apparatus 110 so that control system can monitor the applied pressure using sensors 142 and compare the applied pressure to a target value, as described above in reference to FIGS. 2A and 2B. Alternately, and also similar to control system 50, control system 150 may be configured to receive signals from a remote device, such as a camera described above, which monitors the movement of a person's hand, for example across a surface of the apparatus to see if an area has been wiped, as described above in reference to FIGS. 3A and 3B above. Similarly, as described above to control system 50, control system 150 may include sensors that receive signals from devices, such as near field transmitters, such as RF ID tags, worn by a healthcare worker that provide an indication of where the healthcare worker has wiped to provide an indication of whether a particular surface has been cleaned.

For example, as best seen in FIG. 5, control system 150 includes a computer or controller 152, a memory 154 in communication with the controller 152, a user interface 156, at least one device interface 158, at least one transceiver 160, and sensors 142, for example, sensors for detecting the applied pressure to side rails 136, the headboard 120, the footboard 122, and/or the mattress 16 (or mattress pressure sensing mat 126a).

Optionally, control system 150 may also include load cells 162 for weighing the patient and/or as part of a bed exit system. In the illustrated embodiment shown in FIG. 4, control system 150 further includes a plurality of actuators 168, such as a tilt actuator 168a, a deck actuator 168b, a lift actuator 168c, and a brake actuator 168d. Other actuators may also be included.

The components of control system 150 communicate with each other using conventional electronic communication techniques. In one embodiment, controller 152 communicates with memory 154, user interface 156, sensors 142, and load cells 162 using I-squared-C communications. Other types of serial or parallel communication can alternatively be used. In some other embodiments, different methods may be used for different components. For example, in one embodiment, controller 152 communicates with user interface 156 via a Controller Area Network (CAN) or local Interconnect Network (LIN), while it communicates with memory 154, actuators 168, sensors 142, and load cells 162 using I squared C. Still other variations are possible.

User interface 156 may include a plurality of buttons 164 that a healthcare worker can use to signal to controller 152 that apparatus 110 is going to be cleaned and to initiate the monitoring of the cleaning process described above. This may be achieved using buttons 164 or a touchscreen described above. Further, as described above, it may be done automatically.

In addition, user interface 156 allows a healthcare worker to control various features of the patient support apparatus, such as, but not limited to, raising and lowering the height of frame 116 via lift actuators 168c and/or 168d, pivoting one or more of support surface sections 128 via one or more deck actuators 168b, turning on and off a brake (not shown) via brake actuator 168d, controlling a scale system integrated into the patient support apparatus, controlling an exit alert system integrated into the support apparatus 110, and/or controlling other features of the patient support apparatus 110.

As described above in reference to the previous embodiment, user interface 156 may further include a display 166 integrated therein. Display 166 may comprise a touchscreen display capable of displaying text and/or graphics and sensing the location that a user's finger touches the display, although it will be understood that display 166 could be modified to be a normal LCD display without touchscreen capabilities that instead use hard or soft buttons to interact therewith, or still other types of displays. Further, as described above, interface 156, such as display 166, may be configured to provide a menu for selecting features, including a start button to initiate the monitoring of the cleaning process. Display 166 may also include icons to indicate when a feature is being used, as well as a dynamic icon or icons that illustrate what surfaces have been cleaned or a cleaning status—for example, whether a surface has been adequately cleaned or not. The icon may include a map of the surface to be cleaned with regions that change in response to being wiped (whether detected by motion or pressure). See above for further details.

Optionally, before initializing the monitoring of the cleaning process, controller 152 may confirm that the patient support apparatus is not occupied, either by checking signals from load cells 162 or by checking to see if there is a patient in the vicinity of the patient support apparatus, for example, by checking to see if control system 150 can detect a near field transmitter worn by the patient. This information may be used to control an automatic monitoring system, as noted above.

Controller/computer 152 may include one or more microcontrollers, microprocessors, and/or other programmable electronics that are programmed to carry out the functions described herein. It will be understood that controller 152 may also include other electronic components that are programmed to carry out the functions described herein, or that support the microcontrollers, microprocessors, and/or other electronics. The other electronic components include, but are not limited to, one or more field programmable gate arrays, systems on a chip, volatile or nonvolatile memory, discrete circuitry, integrated circuits, application specific integrated circuits (ASICs) and/or other hardware, software, or firmware, as would be known to one of ordinary skill in the art. Such components can be physically configured in any suitable manner, such as by mounting them to one or more circuit boards, or arranging them in other manners, whether combined into a single unit or distributed across multiple units. Such components may be physically distributed in different positions on patient support apparatus 110, or they may reside in a common location on patient support apparatus 110. When physically distributed, the components may communicate using any suitable serial or parallel communication protocol, such as, but not limited to, CAN, LIN, Firewire, I-squared-C, RS-232, RS-485, etc.

Sensors 142 may, in some embodiments, be any conventional load cells, or similar force measuring sensors, that are positioned to detect the amount of downward force exerted on apparatus 110. For example, sensors 142 may be located in siderails 136 by patient support deck 118, in mattress 126, in mattress sensing mat 126a, in headboard 120 and/or footboard 122 and any other surface that requires or is desirable to have a cleaning confirmation. Controller 152 is in communication with each of the sensors 142, receives the outputs from sensors 142, and then analyzes the signals based on the software program described above.

Interface 158 may also be used to communicate with one or more of the load cells, including for example, with sensors on mattress 126. Mattress 126 may be a mattress of the type disclosed in commonly assigned U.S. patent application Ser. No. 13/836,813, filed Mar. 15, 2013, and Ser. No. 14/308,131, filed Jun. 18, 2014, entitled INFLATABLE MATTRESS AND CONTROL METHODS (STR03A P-400B) and PATIENT SUPPORT (STR03A P-405B), respectively, the complete disclosures of both of which are hereby incorporated herein by reference. Such mattresses include a plurality of inflatable bladders whose inflation pressure is controllable by one or more controllers contained with the mattress. The mattress may further include a plurality of sensors used for detecting information about the status of the mattress, such as, but not limited to, one or more depth sensors, fluid pressure sensors, temperature sensors, patient interface pressures sensors, and/or humidity sensors, or may be used to detect information about the patient, such as vital signs, temperature or activity, as well as the noted sensors, which may be located close to the surface of the mattress to sense the applied pressure when a healthcare worker is cleaning the mattress.

Alternately, as noted, interface 158 may be in communication with a mattress sensing mat or pad 126a, which may be positioned on top of, underneath, or integrated into, mattress 126, but beneath the cover. In this manner, the sensing of the applied pressure to the mattress may be achieved using the sensing mat. In one embodiment, the flexible pressure sensing mat is of the type disclosed in commonly assigned PCT patent application serial number PCT/US12/27402, filed Mar. 2, 2012 by Stryker Corporation, and entitled SENSING SYSTEM FOR PATIENT SUPPORTS, the complete disclosure of which is hereby incorporated herein by reference. Such a flexible pressure sensing mat may forward pressure information, including but not limited to, a pressure distribution map, to controller 152, and/or any other information that is detectable by the flexible pressure sensing mat. Further, the sensors or sensing mat may be used for other purposes, such as detecting the pressure interface with a patient supported on the mattress 126, patient heart rate, patient respiration rate, patient position, patient orientation, patient movement—including patient turns, and other information.

In some embodiments, interface 158 is a Controller Area Network connection that communicates with mattress 126, while in other embodiments, interface 158 takes on other forms. In one embodiment, interface 158 is a wireless connection, such as that disclosed in commonly assigned U.S. patent application Ser. No. 13/296,656, filed by applicants Guy Lemire et al. and entitled PATIENT SUPPORT WITH WIRELESS DATA AND/OR ENERGY TRANSFER, issued on Oct. 21, 2014 as U.S. Pat. No. 8,864,205, the complete disclosure of which is hereby incorporated herein by reference.

In still other embodiments, control system 150 may include a transceiver, such as a near field communications transceiver, which can communicate with the camera noted above to receive the camera signals, which are used by controller 152 to determine whether movement by a healthcare worker is consistent with the healthcare worked cleaning the surface of interest.

Alternately, interface 158 may be in communication with the sensors or camera based on input from controller 152. Controller 152 may receive input from user interface 156 or from user interfaces 156b, which are mounted in, for example, the head end side rails 136a, 136c. User interfaces 156a may be provided on each of the inwardly facing sides of head end side rails 136a, 136c, for use by a patient, while user interface 156b may be provided on each of the outwardly facing side of head end side rails 36a, 36c for use by a healthcare worker. Interface 158 may communicate wirelessly or through a wired connection. In one embodiment, as noted above, controller 152 may receive input remotely from the patient support apparatus. For example, controller 152 may receive the input from a hand held device, a nurse call station, or through the hospital network (more fully described below). User interfaces 156b and/or hand held device 126 may be used to by a healthcare worker to initiate the monitoring of the cleaning cycle, in addition to any of the control features described above.

In addition to generating a local indication that the cleaning process is or is not complete, controller 152 may be in communication with one or more remote devices, including one or more networks. For example, as shown in FIG. 5, apparatus 110 may include a transceiver 160 that may be used by controller 152 for forwarding a notification and/or information from control system 150 to other devices, such as a healthcare facility computer network, or another recipient. The healthcare facility computer network is often, though not necessarily always, an Ethernet, and it will be understood that the healthcare facility computer network can take on other forms. In one embodiment, transceiver 160 is a WiFi radio transmitter and receiver that is capable of communicating with a wireless access point of the hospital network in accordance with IEEE 802.11 standards, or in accordance with other standards. For more details about a suitable communication system, reference is made to U.S. patent application Ser. No. 14/211,613, filed on Mar. 14, 2014, by Michael Joseph Hayes, et al., entitled PATIENT SUPPORT APPARATUS WITH REMOTE COMMUNICATIONS, (STR03 R&D P-414B).

In one embodiment, one or more software applications, such as monitoring applications, may be provided at support apparatus 110 (as thin client, fat client, or local applications) that record the cleaning process and the frequency of the cleaning events. This information may be forwarded by the application to a corresponding network service of a third party, for example, a third party cleaning service or other third party including an insurance carrier. This may be used for billings, studies etc., for example to assess the efficacy of a cleaning process, for example, for a given apparatus.

In one embodiment, control system 150 may include a near field communications transceiver that communicates in any of the manners, and with any of the devices, disclosed in commonly assigned U.S. patent application Ser. No. 13/802,992, filed Mar. 14, 2013 by applicants Michael Hayes et al, and entitled COMMUNICATION SYSTEMS FOR PATIENT SUPPORT APPARATUSES (STR03 R&D P-397A), the complete disclosure of which is hereby incorporated herein by reference. Further, the near field communications transceiver can be used for establishing an association between a medical apparatus, such as apparatus 110 and a healthcare worker. For example, the healthcare worker may wear a badge, such as an RF ID tag, which allows the controller to track, for example, how long the healthcare worker was present during the cleaning cycle and the identity of the healthcare worker.

In addition to near field communications, interface 158 may also carry out far field communications using one or more transceivers that are separate from transceivers 160. Such separate transceivers typically communicate using a separate communications protocol than that of transceiver 160. For example, in one embodiment, transceiver 160 using WiFi communications, while the one or more transceivers of interface 158 use Bluetooth and/or ZigBee communications, or other protocols.

When patient support apparatus 10 or 110 is implemented as a recliner, it may be a recliner such as that disclosed in commonly assigned U.S. patent application Ser. Nos. 14/212,417, 14/212,009, 14/212,323, and 14/212,253 (STR03D P-410A, 410B, 410C, 410D), filed Mar. 14, 2013, by applicant Richard Derenne and entitled MEDICAL SUPPORT APPARATUS, respectively, the complete disclosure of which is incorporated herein by reference. Other types of recliners may, of course, be used.

Various alterations and changes can be made to the above-described embodiments without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

We claim:

1. A surface cleaning assistance system comprising:
   a sensor mounted relative to a surface, the sensor configured to detect pressure applied to the surface, the sensor generating sensor signals based on the detected pressure;
   a user interface mounted relative to the surface and configured to generate an indication associated with the surface being cleaned; and
   a controller in communication with the sensor and the user interface, the controller having stored therein a cleaning target value, the controller configured to receive the sensor signals from the sensor, to compare the sensor signals to the cleaning target value, and to generate an output signal associated with the sensor signals, the indication changing in response to the output signal and indicating when (1) a pressure applied to the surface is below the cleaning target value, (2) a pressure applied to the surface is at the cleaning target value, or (3) a pressure applied to the surface is above the cleaning target value, wherein the indication provides feedback at the surface to a person cleaning the surface;
   wherein the surface comprises a surface of a medical apparatus; and
   wherein said medical apparatus comprises a hospital bed, the user interface being provided at the hospital bed, the user interface comprising a display at the hospital bed, the display generating an image representing the surface of the hospital bed, and the image changing in response to the output signal wherein the image provides the feedback to a person cleaning the surface.

2. The surface cleaning assistance system according to claim 1, wherein the image comprises a map of at least a portion of the hospital bed.

3. The surface cleaning assistance system according to claim 2, the sensor comprising a first sensor, further comprising a second sensor, the controller in communication with the sensors and evaluating the sensor signals from each of the sensors.

4. The surface cleaning assistance system according to claim 3, wherein each of the sensors is associated with a region of the surface.

5. The surface cleaning assistance system according to claim 1, further comprising a transmitter, the transmitter in communication with the controller for sending the output signal from the controller to a remote device.

6. The surface cleaning assistance system according to claim 1, wherein the sensor comprises a load cell.

7. The surface cleaning assistance system according to claim 1, the user interface being configured to initiate the controller monitoring the sensor signals.

8. The surface cleaning assistance system according to claim 1, further comprising a timer, the controller including or being in communication with the timer, the controller determining the time spent by a user cleaning the surface using the timer.

9. A surface cleaning assistance system comprising:
   a sensor mounted relative to a surface, the sensor configured to detect pressure applied to the surface, the sensor generating sensor signals based on the detected pressure;
   a controller in communication with the sensor and having stored therein a cleaning target value, the controller configured to receive the sensor signals from the sensor, to compare the sensor signals to the cleaning target value, and to generate an output signal associated with the sensor signals, the output signal indicating whether said sensor signals indicate a pressure below, at, or above the cleaning target value; and
   a display, the display in communication with the controller and generating an image, the image being responsive to the output signal, the image comprising a map of at least a portion of the surface, the sensor comprising a first sensor, further comprising a second sensor, the controller in communication with the first and second sensors and evaluating the sensor signals from each of the sensors, wherein each sensor is associated with a region of the surface, and the map is segmented into zones with each zone corresponding to and having an icon representing one region of the regions of the surface.

10. The surface cleaning assistance system according to claim 9, wherein the controller changes the icon associated with the one region when the controller determines that the sensor signals associated with the one region indicates for the one region changes in pressure from below, at, or above the target value for the one region.

11. A surface cleaning assistance system comprising:
a sensor mounted relative to a surface, the sensor configured to detect movement across the surface, the sensor generating sensor signals based on the detected movement across the surface;
a user interface mounted relative to the surface and configured to generate an indication associated with the surface being cleaned; and
a controller in communication with the sensor and the user interface, the controller having stored therein a cleaning target area, the controller configured to receive the sensor signals from the sensor and to compare the detected movement to the cleaning target area and generate an output signal associated with the sensor signals, the indication changing in response to the output signal and indicating whether the sensor signals indicate when (1) the movement covers the cleaning target area or (2) the movement does not cover the cleaning target area wherein the indication provides feedback at the surface to a person cleaning the surface, the user interface comprising a display in communication with the controller, and the display displaying an image based on the output signal wherein the image provides feedback to a person cleaning the surface.

12. The surface cleaning assistance system according to claim 11, wherein the surface comprises a surface of an apparatus, such as a medical apparatus, including a hospital bed, a stretcher, an OR table, or a cot.

13. The surface cleaning assistance system according to claim 11, wherein said image comprises a map of at least a portion of the cleaning target area.

14. The surface cleaning assistance system according to claim 11, wherein the image includes a plurality of regions, the controller changing one of the regions when the controller determines that the sensor signals associated with the one region indicate for the one region a change between the movement covering or not covering the cleaning target area.

15. The surface cleaning assistance system according to claim 11, further comprising a transmitter, the transmitter in communication with the controller for sending the output signal from the controller to a remote device.

16. The surface cleaning assistance system according to claim 11, wherein the user interface is configured to initiate the controller evaluating the sensor signals.

17. The surface cleaning assistance system according to claim 11, wherein the sensor comprises a camera.

18. The surface cleaning assistance system according to claim 11, further comprising a cleaning apparatus, and the sensor detecting the movement of the cleaning apparatus.

* * * * *

UNITED STATES PATENT AND TRADEMARK OFFICE
CERTIFICATE OF CORRECTION

PATENT NO. : 9,922,533 B2
APPLICATION NO. : 14/947637
DATED : March 20, 2018
INVENTOR(S) : Michael Joseph Hayes and Anuj K. Sidhu Page 1 of 1

It is certified that error appears in the above-identified patent and that said Letters Patent is hereby corrected as shown below:

On the Title Page

Item (71) Applicant:
"Stryker Corporation, Kalmazoo, FL (US)"
Should be:
-- Stryker Corporation, Kalamazoo, MI (US) --

Signed and Sealed this
Twenty-first Day of August, 2018

Andrei Iancu
*Director of the United States Patent and Trademark Office*